US008141522B2

(12) United States Patent
Askinasi

(10) Patent No.: US 8,141,522 B2
(45) Date of Patent: Mar. 27, 2012

(54) SCENT DISTRIBUTING DECORATIVE STONE

(75) Inventor: Barry Askinasi, Mt. Sinai, NY (US)

(73) Assignee: Four Paws Products, Ltd., Hauppauge, NY (US)

( * ) Notice: Subject to any disclaimer, the term of this patent is extended or adjusted under 35 U.S.C. 154(b) by 38 days.

(21) Appl. No.: 12/862,367

(22) Filed: Aug. 24, 2010

(65) Prior Publication Data

US 2012/0048210 A1 Mar. 1, 2012

(51) Int. Cl.
*A01K 29/00* (2006.01)

(52) U.S. Cl. .............................. 119/712; 119/174; 52/4

(58) Field of Classification Search .................. 119/712, 119/711, 161, 174; 47/41.1, 48.5; 52/4, 52/155, 301; 135/118; 43/131
See application file for complete search history.

(56) References Cited

U.S. PATENT DOCUMENTS

| 3,916,564 | A | * | 11/1975 | Crowell, Sr. ................... 47/48.5 |
| 4,350,296 | A | * | 9/1982 | Kuhlman et al. ............. 239/201 |
| 4,927,118 | A | * | 5/1990 | Pierorazio ..................... 248/545 |
| 5,048,240 | A | * | 9/1991 | Dupre et al. ......................... 52/4 |
| 5,379,545 | A | * | 1/1995 | Gall et al. ....................... 43/131 |
| 5,918,410 | A | * | 7/1999 | Knuppel ......................... 43/131 |
| 6,192,621 | B1 | | 2/2001 | Fain |
| 6,241,161 | B1 | | 6/2001 | Corbett |
| 6,796,082 | B1 | * | 9/2004 | Duston et al. .................. 43/131 |
| 7,051,681 | B2 | | 5/2006 | Pope |
| 2004/0099300 | A1 | * | 5/2004 | Warren ......................... 135/118 |
| 2009/0266307 | A1 | * | 10/2009 | LaPlant et al. ................ 119/712 |
| 2009/0288357 | A1 | * | 11/2009 | Kubicek .......................... 52/301 |

* cited by examiner

*Primary Examiner* — Kristen Hayes
(74) *Attorney, Agent, or Firm* — Grossman, Tucker, Perreault & Pfleger, PLLC

(57) ABSTRACT

A molded decorative yard stake having a basin for containing an animal attractant and a cover removeably locking in place over, and sufficiently spaced from, the basin to permit gradual aerosolization of the animal attractant.

5 Claims, 4 Drawing Sheets

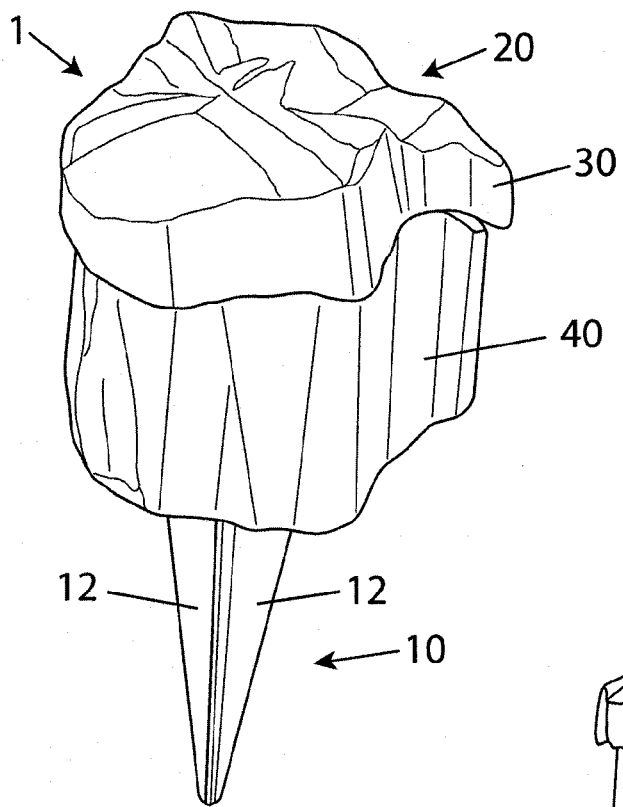
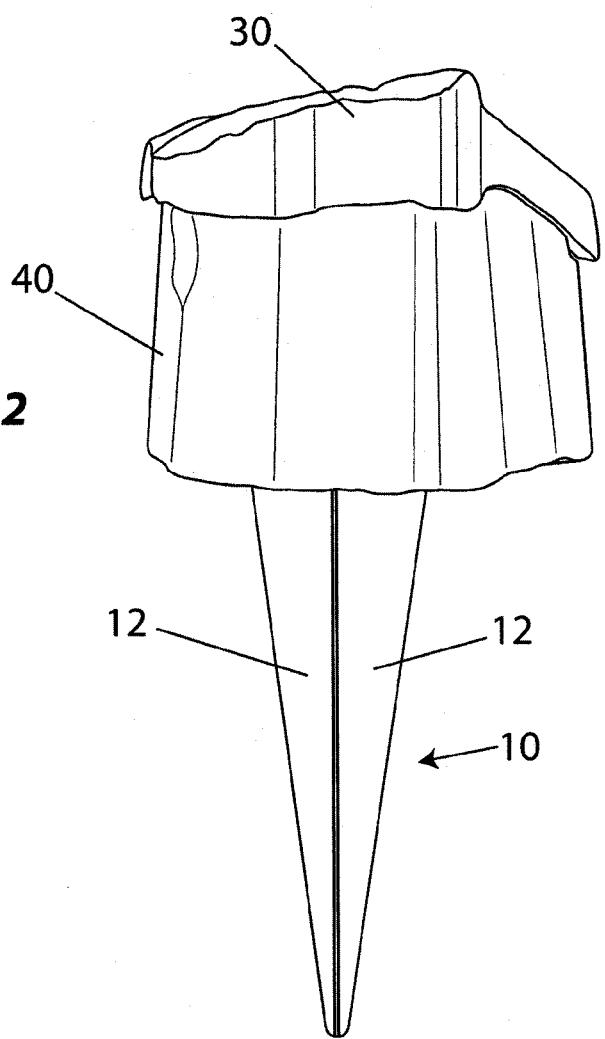

SCENT DISTRIBUTING DECORATIVE STONE

FIELD OF THE INVENTION

The invention relates to a device for training canines to eliminate waste in specific areas. More particularly, a molded decorative stake contains an openable reservoir for containing liquid pheromones used to influence the location that canines eliminate waste.

BACKGROUND OF THE INVENTION

One of the perennial problems for dog owners is in controlling where the animal eliminates waste. Animal waste can contain excessive amounts of nitrogen that essentially "burns" grass and other vegetation, similar to excessively fertilizing an area. While a proper amount of nitrogen is necessary for healthy plants, an excessive amount will damage and even kill the plants. The result is that the area of the lawn that an animal frequents for elimination of waste will turn brown and the area may become devoid of grass or other plant life.

Several approaches have been taken by pet owners in dealing with this problem. One method is to treat the area that the animal frequents by, for example, diluting the waste with water. Other potential methods of treatment are by removing the animal waste or re-seeding the area. However, these methods tend to be time consuming, labor intensive and may be ineffective if the animal repeatedly frequents the area. Another method of addressing the problem is by training the animal to eliminate waste in specific acceptable locations. Such locations may be where there is little or no vegetation, such as on woodchips or other non-seeded locations. The problem faced by animal owners is in consistently having the animal eliminate in such specific location.

Various methods may be used in training an animal to use a specific area for elimination. Training and behavior modification are one example. Another known method is to place animal attractants such as pheromones in the specific area of interest to encourage the animal to use that area. The considerations in using attractants is to provide a method of dispensing it that permits the scent to be disbursed consistently over an extended period of time, limiting access to the scent producing substance by the animal, easy access to the compartment for holding the scent producing substance so that it may be easily refilled and having a pleasing appearance to the device.

It is with these considerations in mind that the present invention is contemplated.

BRIEF DESCRIPTION OF THE DRAWINGS

The foregoing and other features of the present invention will be more readily apparent from the following detailed description and drawings of illustrative embodiments of the invention in which:

FIG. 1 is a top perspective view of the scent producing decorative stone in accordance with one embodiment of the present invention;

FIG. 2 is a side view of the scent producing decorative stone in accordance with one embodiment of the present invention;

DETAILED DESCRIPTION

Figure 3:
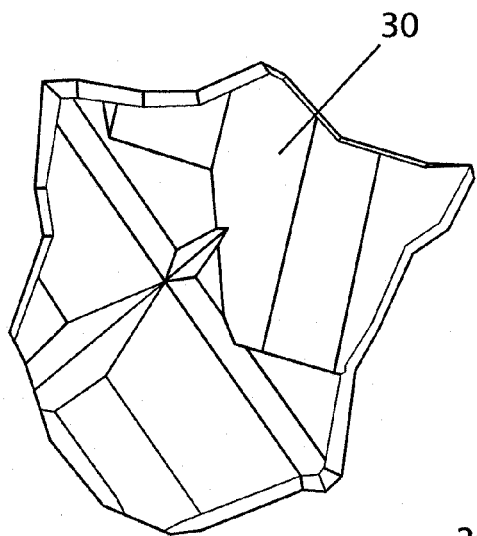
FIG. 3 is a top view of the scent producing decorative stone in accordance with one embodiment of the present invention.

Various embodiments of the present invention will be described in detail with reference to the drawings, where like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention. In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Figure 4:
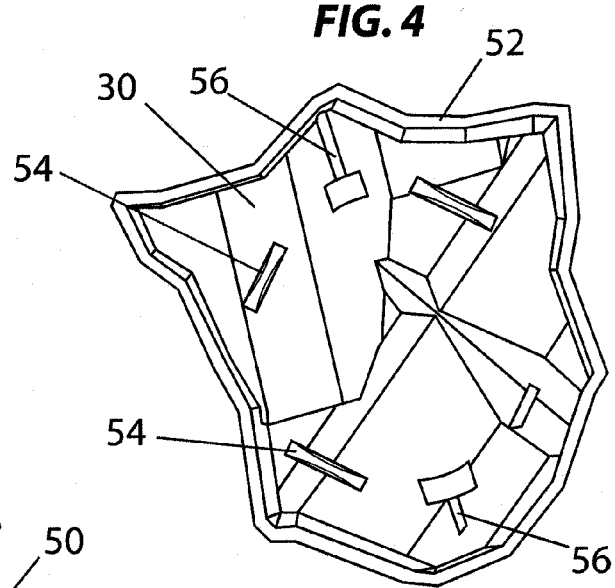
FIG. 4 is a bottom view of the cover of the scent producing decorative stone in accordance with one embodiment of the present invention.
Figure 5:
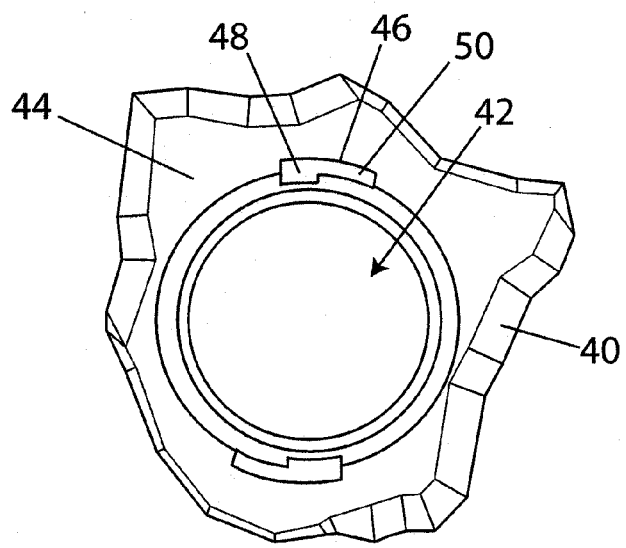
FIG. 5 is a top view of the housing of the scent producing decorative stone in accordance with one embodiment of the present invention.
Figure 6:
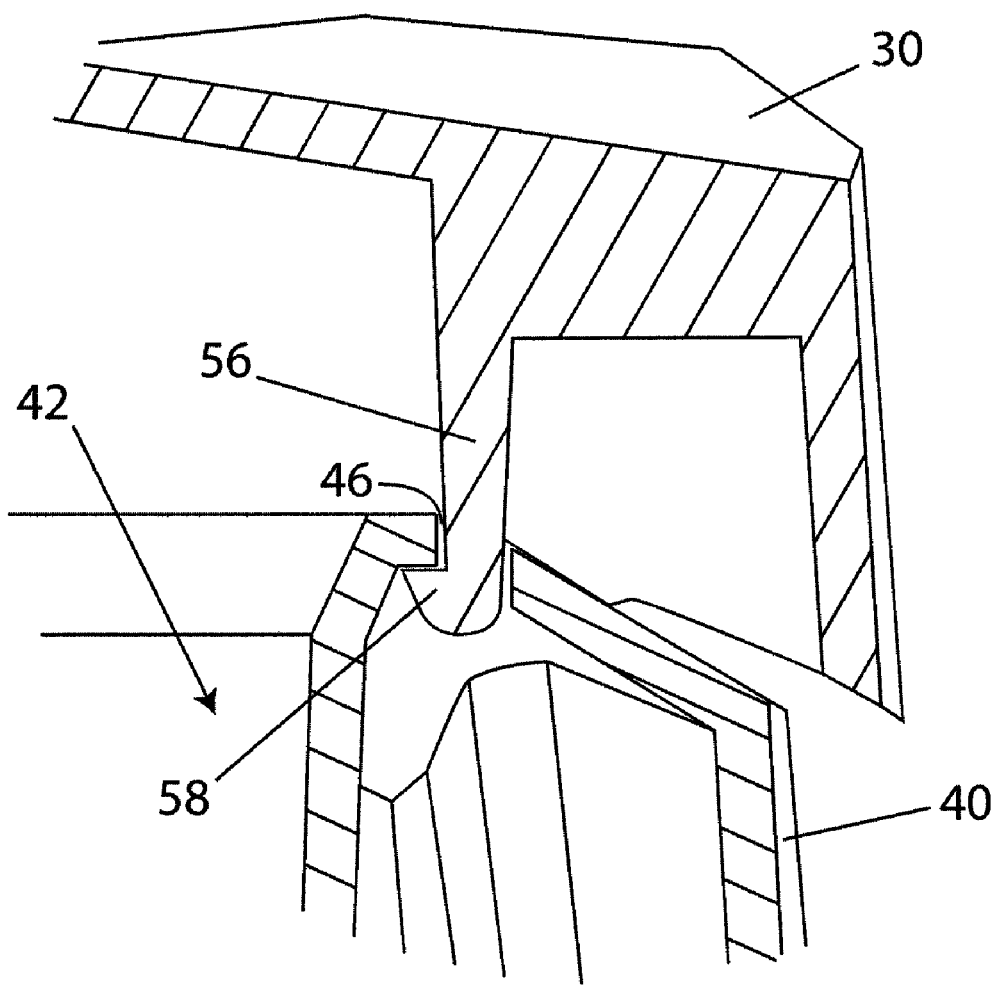
FIG. 6 is a sectional view of a portion of the scent producing decorative stone in accordance with one embodiment of the present invention.
Figure 7:
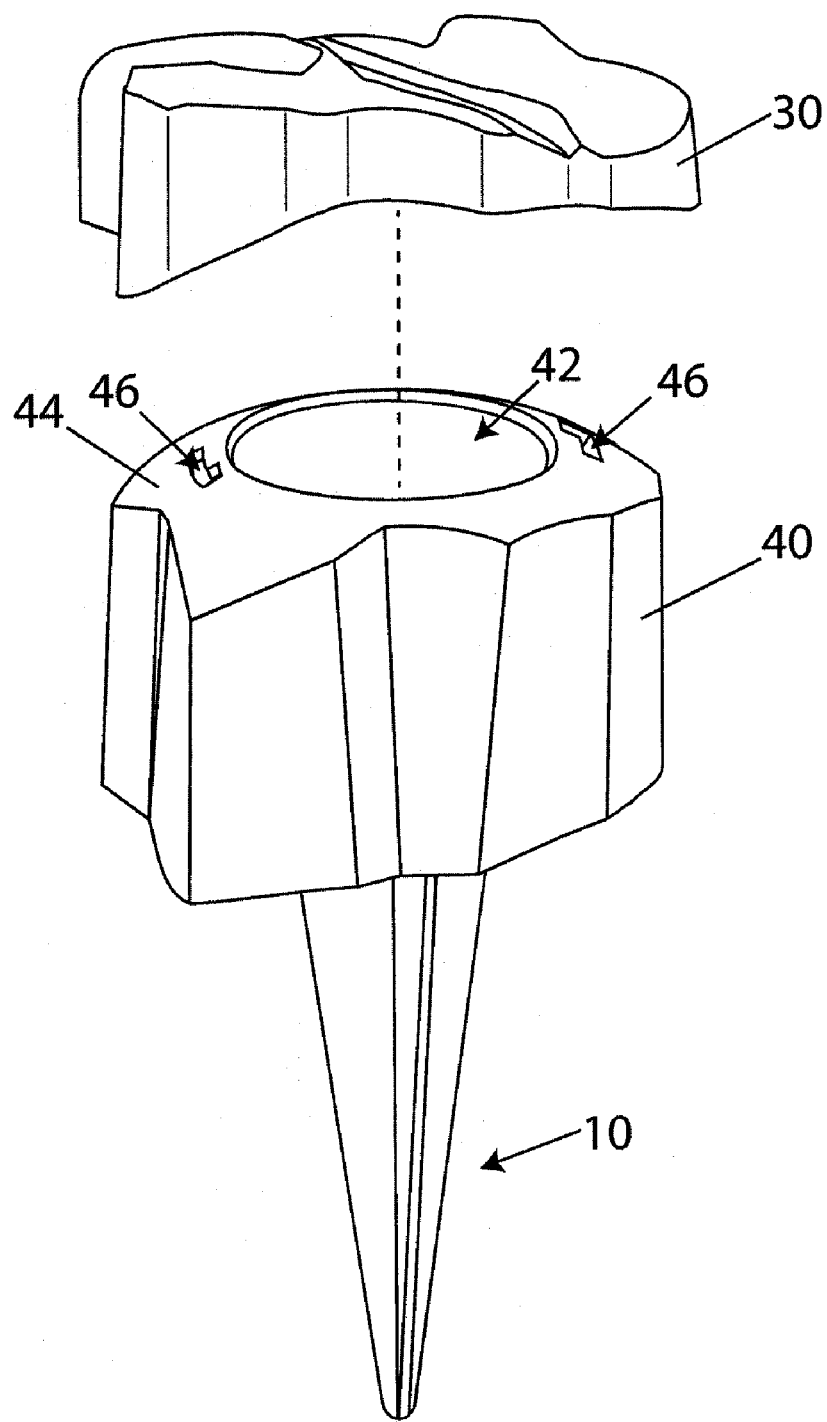
FIG. 7 is a perspective view with the cover separated from the housing of the scent producing decorative stone in accordance with one embodiment of the present invention.

Scent producing decorative stone 1 is shown in FIGS. 1 through 7. Scent producing decorative stone 1 is comprised of stake 10 and housing 20. Stake 10 may consist of two or more blades 12. Preferably, blades 12 will be oriented at a ninety degree angle from one another. This orientation provides greater structural support for stake 10 and, when inserted into the ground, provides greater resistance against movement in multiple directions. Blades 12 can also be in other configurations. For example, stake 10 may have two blades oriented approximately 120 degrees from one another. Stake 10 is tapered from the proximate end that is attached to housing 20 to the distal end that is inserted into the ground.

Housing 20 is attached to the proximate end of stake 10. Housing 20 consists of cover 30 and base 40, and generally takes the form of a stone or rock that may be found in any garden or yard. The outside surface of base 40 preferably will be textured and colored the same as a typical garden stone. The stake and housing may be formed from a number of different materials, but preferably from a durable molded plastic. Stake 10 may also be integrally formed with base 40. Basin 42 (FIG. 5) is formed in the center of base 40 and is capable of containing an animal attractant such as a pheromone, preferably in liquid form. Hook slots 46 are located on top surface 44 of base 40. Hook slots 46 may be arcuately formed with wide section 48 that permits a prong of a male extension to pass through it, and a narrow section 50 that has a width that prevents the prong of a male extension from passing through it. Hook slots 46 have the wide and narrow sections oriented the same way for each hook slot when moving in either a clockwise or counter-clockwise rotational direction.

Cover 30 is formed to integrate with base 40 to make housing 20 appear like a complete stone or rock. The top surface of cover 30 may have the same texturing and coloring as the exterior surface of base 40. Cover 30 may circumscribe a surface area that is at least the same as or larger than the opening of basin 42. In one embodiment, cover 30 contains cover edging 52 which is formed along a peripheral edge of cover 30 and extends downwardly when cover 30 is placed on top of base 40. When cover 30 is placed over base 40, edging 52 may extend partially below top surface 44 of base 40. In another embodiment, when cover 30 is placed over base 40, edging 52 is spaced slightly above top surface 44.

To maintain a minimum spacing between cover 30 and base 40, cover 30 contains spacers 54 that contact top surface 44 when the cover is placed over the base. In one embodiment, three spacers are integrally formed with cover 30, are spaced inwardly from the peripheral edges of the cover and extend downward. Spacers 54 may be structured so that they may slide across top surface 44 as cover 30 is rotated to be locked in place. Cover 30 also contains male extensions 56 that are connected to cover 30 at a first proximal end and prongs 58 at the distal ends. Prongs 58 are sized to fit through wide section 48 of hook slots 46 but unable to pass through narrow section 50. The location, shape and size of the spacers and male extensions may be in a number of different configurations. For example, spacers 54 may extend upwards from top surface 44 towards cover 30.

To close scent producing decorative stone 1, cover 30 is placed over base 40. Prongs 58 are aligned with and inserted through wide section 48 of hook slots 46. Any number of prongs may be used. Spacers 54 engage top surface 44 to hold cover 30 at a minimum distance above base 40. Cover 30 is then rotated so that male extension 56 engages narrow section 50 of hook slots 46. Prong 58 will be located below narrow section 50, and engages the underside of top surface 44 at the edge of narrow section 50. In this manner, male extension 56 and hook slots 46 hold the cover a maximum distance from the base. Through the action of spacers 54 holding the cover a minimum distance above the base and prong 58 holding the cover a maximum distance from the base, cover 30 is locked in place over base 40. The use of separate spacers and male extensions for the cover provides stability in holding the cover in place over the base. However, in another embodiment, spacers 54 may be integrated with male extension 56. To obtain the same stability, the number of integrated spacers/male extensions may be increased to three or more.

In use, a pet owner picks a location that they would like to train their pet to eliminate waste. Scent producing decorative stone is then inserted into the ground. Base 40 may be partially buried in the ground. Cover 30 may be removed by rotating the cover to disengage male extension 56 and prong 58 from hook slots 46. The pet owner may then place an animal attractant, such as a pheromone or other scent-producing substance, into basin 42. Cover 30 is then re-attached to housing 20.

The length of male extension 56, spacers 54 and the size and shape of cover edging 52 are chosen so as to permit the gradual aerosolization of the animal attractant over time. Preferably, the animal attractant would only have to be added or supplemented periodically, for example once per week or once per month. The animal attractant would be released from basin 42 by passing through the spacing between cover 30 and housing 20. However, cover 30 and the spacing between the cover and housing would also be configured to prevent water from entering basin 42, as by example from rain or watering of the lawn. The configuration would also prevent unwanted access to the animal attractant by the pet or other small animals.

While the invention has been particularly shown and described with reference to preferred embodiments thereof, it will be understood by those skilled in the art that various changes in form and details may be made therein without departing from the spirit and scope of the invention.

The invention claimed is:

1. A yard ornament for modifying canine behavior comprising:

a stake having at least two blades, with a face of one of the blades forming an angle less than 180 degrees with a face of a second blade; and a stone-shaped molded housing connected to the stake, the molded housing having, a base with a centrally located basin capable of containing liquid canine attractant and extending below a top surface of the base, the base having two or more hook slots located on the top surface of the base substantially adjacent to the basin, each of the hook slots having a width that narrows along a length of the hook slots in one rotational direction around the basin, a cover removably coupled to the base, two or more male extensions with proximate and distal ends, the proximate ends being attached to the cover and the distal ends containing prongs, two or more spacers attached to an underside of the cover, substantially parallel to the two or more male extensions and having a length that is less than the male extensions, and the male extensions and spacers being attached to the cover such that when the cover is placed on the base, the spacers contact the top surface of the base and the prongs of the male extensions extend into the hook slots on the top surface of the base, wherein when the cover is moved in the one rotational direction the prongs engage a bottom of the top surface of the base to lock the cover in place spaced apart from the base by the spacers.

2. The yard ornament of claim 1, further comprising:

canine attractant contained in the basin of the stone-shaped molded housing.

3. The yard ornament of claim 1, wherein the cover has a top surface area that is the same as or greater than a top surface area of the base.

4. The yard ornament of claim 1, wherein the base and cover are configured to be sufficiently spaced apart so that canine attractant contained within the basin releases over an extended period of time through the space between the base and cover.

5. The yard ornament of claim 1, wherein the cover contains a cover edging that extends below the top surface of the base when the cover is locked onto the base.

* * * * *